(12) United States Patent
Chen et al.

(10) Patent No.: US 11,823,390 B2
(45) Date of Patent: Nov. 21, 2023

(54) METHOD AND DEVICE FOR PLANARIZING THREE-DIMENSIONAL DATA OF BRAIN, AND COMPUTER-READABLE STORAGE MEDIUM

(71) Applicant: BEIJING GMINE VISION TECHNOLOGIES LTD., Beijing (CN)

(72) Inventors: Wei Chen, Beijing (CN); Yuxue Ren, Beijing (CN); Boyang Wu, Beijing (CN)

(73) Assignee: BEIJING GMINE VISION TECHNOLOGIES LTD., Beijing (CN)

(*) Notice: Subject to any disclaimer, the term of this patent is extended or adjusted under 35 U.S.C. 154(b) by 14 days.

(21) Appl. No.: 17/773,932

(22) PCT Filed: Nov. 4, 2020

(86) PCT No.: PCT/CN2020/126489
§ 371 (c)(1),
(2) Date: May 3, 2022

(87) PCT Pub. No.: WO2021/088869
PCT Pub. Date: May 14, 2021

(65) Prior Publication Data
US 2022/0366528 A1 Nov. 17, 2022

(30) Foreign Application Priority Data

Nov. 5, 2019 (CN) .......................... 201911068702.2
Mar. 27, 2020 (CN) .......................... 202010226115.8
Oct. 20, 2020 (CN) .......................... 202011126641.3

(51) Int. Cl.
*G06T 15/00* (2011.01)
*G06T 7/12* (2017.01)
(Continued)

(52) U.S. Cl.
CPC ................ *G06T 7/12* (2017.01); *G01R 33/48* (2013.01); *G06T 3/0012* (2013.01);
(Continued)

(58) Field of Classification Search
CPC .. G06T 7/66; G06T 7/521; G06T 7/12; G06T 7/62; G06T 15/10; G06T 19/00;
(Continued)

(56) References Cited

U.S. PATENT DOCUMENTS 9,972,128 B2 * 5/2018 Gregson ................. G06T 15/08
2013/0066219 A1 * 3/2013 Jiang .................. A61B 5/02007
600/504
(Continued)

FOREIGN PATENT DOCUMENTS

| CN | 109410195 A | 3/2019 |
| CN | 109416939 A | 3/2019 |

(Continued)

OTHER PUBLICATIONS

Shen Y, Gao M. Brain tumor segmentation on MRI with missing modalities. InInformation Processing in Medical Imaging: 26th International Conference, IPMI 2019, Hong Kong, China, Jun. 2-7, 2019, Proceedings 26 2019 (pp. 417-428). Springer In.*

(Continued)

*Primary Examiner* — Phu K Nguyen
(74) *Attorney, Agent, or Firm* — The PL Law Group, PLLC

(57) ABSTRACT

A method of planarizing three dimensional data of a brain implemented by a computer according to an embodiment of the present disclosure includes acquiring a three-dimensional model of the brain scanned by a scanning device, the three-dimensional model including the three-dimensional data of the brain, and mapping, in the computer, the three-dimensional model onto a circle in an area-preserving man- (Continued)

ner to form an area-preserving map. The method can convert a three-dimensional brain model into a circle or unit disc on a two-dimensional plane so that the brain model can be compared with a reference brain model, and a doctor can judge the position and degree of a brain lesion more accurately.

17 Claims, 8 Drawing Sheets

(51) Int. Cl.
| | |
|---|---|
| G06T 7/149 | (2017.01) |
| G16H 30/20 | (2018.01) |
| G06T 17/20 | (2006.01) |
| G06T 19/20 | (2011.01) |
| G06T 7/62 | (2017.01) |
| G06T 7/11 | (2017.01) |
| G06T 7/66 | (2017.01) |
| G06T 7/13 | (2017.01) |
| G06T 7/70 | (2017.01) |
| G16H 30/40 | (2018.01) |
| G01R 33/48 | (2006.01) |
| G06T 3/00 | (2006.01) |
| G06T 7/521 | (2017.01) |

(52) U.S. Cl.
CPC .......... *G06T 3/0031* (2013.01); *G06T 3/0037* (2013.01); *G06T 7/11* (2017.01); *G06T 7/13* (2017.01); *G06T 7/149* (2017.01); *G06T 7/521* (2017.01); *G06T 7/62* (2017.01); *G06T 7/66* (2017.01); *G06T 7/70* (2017.01); *G06T 17/20* (2013.01); *G06T 19/20* (2013.01); *G16H 30/20* (2018.01); *G16H 30/40* (2018.01); *G06T 2200/08* (2013.01); *G06T 2207/10024* (2013.01); *G06T 2207/10028* (2013.01); *G06T 2207/10081* (2013.01); *G06T 2207/10088* (2013.01); *G06T 2207/10108* (2013.01); *G06T 2207/20021* (2013.01); *G06T 2207/30016* (2013.01); *G06T 2207/30028* (2013.01); *G06T 2210/41* (2013.01); *G06T 2219/2008* (2013.01); *G06T 2219/2021* (2013.01)

(58) Field of Classification Search
CPC ... G06T 7/13; G06T 7/11; G06T 17/20; G06T 3/0037; G06T 7/0012; G06T 19/20; G06T 3/0031; G06T 7/70; G06T 7/149; G06T 3/0012; G06T 2207/30016; G06T 2210/41; G06T 2207/10108; G06T 2200/08; G06T 2219/2021; G06T 2207/10024; G06T 2219/021; G06T 2207/10028; G06T 2207/30028; G06T 2207/10081; G06T 2207/20021; G06T 2207/10088; G06T 2219/2008; G16H 50/20; G16H 30/20; G16H 30/40; G16H 50/50; G01R 33/48; G01R 33/5608; A61B 6/5211; A61B 6/032; A61B 6/50; A61B 6/5217; A61B 6/037
USPC ........................................................ 345/418
See application file for complete search history.

(56) References Cited

U.S. PATENT DOCUMENTS

| | | | |
|---|---|---|---|
| 2019/0259202 A1 | 8/2019 | Gabriel et al. | |
| 2019/0270118 A1* | 9/2019 | Araujo-Simon | G06F 15/16 |
| 2022/0351388 A1* | 11/2022 | Chen | G16H 30/20 |
| 2022/0366528 A1* | 11/2022 | Chen | G06T 7/66 |

FOREIGN PATENT DOCUMENTS

| | | |
|---|---|---|
| CN | 110766808 A | 2/2020 |
| CN | 111127314 A | 5/2020 |
| WO | WO 2004/044689 A2 | 5/2004 |

OTHER PUBLICATIONS

Havaei M, Larochelle H, Poulin P, Jodoin PM. Within-brain classification for brain tumor segmentation. International journal of computer assisted radiology and surgery. May 2016;11:777-88.*
Yau et al, Chinese document CN 1781111 (English translation), May 2006.*
Wu MN, Lin CC, Chang CC. Brain tumor detection using color-based k-means clustering segmentation. InThird international conference on intelligent information hiding and multimedia signal processing (IIH-MSP 2007) Nov. 26, 2007 (vol. 2, pp. 245-250). IEEE.*
Chen et al., CN 11127314 Chinese document (English translation), May 2020.*
Tu Z, Bai X. Auto-context and its application to high-level vision tasks and 3d brain image segmentation. IEEE transactions on pattern analysis and machine intelligence. Dec. 1, 2009;32(10):1744-57.*
International Search Report for PCT/CN2020/126489 dated Feb. 8, 2021.

* cited by examiner

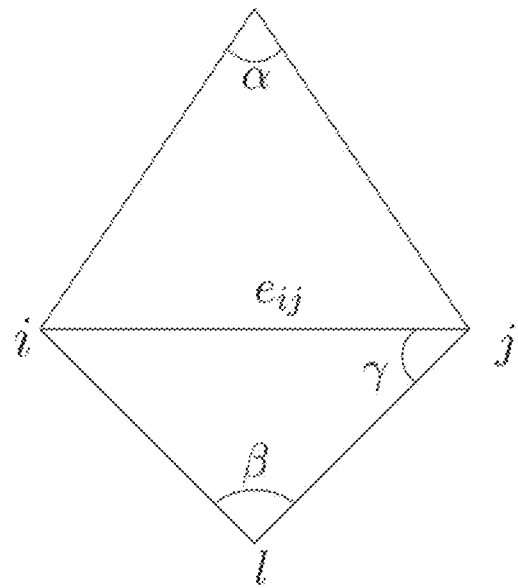

FIG. 8 initializing the second weight of each harmonic mapping point, wherein at least three harmonic mapping points form one initial face — S6301 determining weighted dual points of each initial face, the weighted dual points having equal weighted distances to vertices of each initial face, wherein the weighted dual points are connected to form a dual face of the weighted dual points, and a plurality of weighted dual faces determine a weighted Voronoi diagram — S6303 updating the second weight of each harmonic mapping point and readjusting the weighted Voronoi diagram according to the updated second weight — S6305

FIG. 9 determining a center of gravity of each dual face in the weighted Voronoi diagram — S6401 mapping each of the harmonic mapping points to the center of gravity of each dual face, thereby mapping the three-dimensional model to the circle in the area-preserving manner — S6403

METHOD AND DEVICE FOR PLANARIZING THREE-DIMENSIONAL DATA OF BRAIN, AND COMPUTER-READABLE STORAGE MEDIUM

CROSS-REFERENCE TO RELATED APPLICATIONS

This application claims benefit under 35 U.S.C. 119, 120, 121, or 365(c), and is a National Stage entry from International Application No. PCT/CN2020/126489, filed Nov. 4, 2020, which claims priority to the benefit of Chinese Patent Application Nos. 201911068702.2 filed on Nov. 5, 2019, 202010226115.8 filed on Mar. 27, 2020 and 202011126641.3 filed on Oct. 20, 2020 in the Chinese Intellectual Property Office, the entire contents of which are incorporated herein by reference.

BACKGROUND

1. Technical Field

This disclosure relates generally to the field of iconology, and more particularly, to the field of medical imaging.

2. Background Art

Many diseases in human are associated with brain, for example, when certain regions of the brain become diseased, a disease in certain limb parts of a patient will be caused. For example, suffering an Alzheimer's disease (AD) will result in death of brain nerve cells and damage of brain tissue. During suffering the disease, the brain will atrophy significantly so that all functions are affected. In the case of a severe Alzheimer's disease, a cerebral cortical area atrophies, and the regions damaged include a thought region, a planning region, and a memory region; hippocampus is a main region where a new memory is formed and is also a region where specially severe atrophy occurs; and a fluid-filled space in a ventricle will become larger.

In the prior art, through CT (thin layer scanning) and MRI (coronal) examination, it can be showed that the cerebral cortex atrophy is obvious, particularly the hippocampus and medial temporal lobe, which can be used for clinical diagnosis of AD. Compared to the CT, the MRI is more sensitive to detecting a subcortical vascular change (e.g., infarction in a key part) and prompting a change of a special disease (e.g., multiple sclerosis, progressive supranuclear palsy, multiple system atrophy, corticobasal degeneration, prion disease, frontotemporal dementia, etc.).

However, for such detection in the prior art, a judgment is made on the basis of layered scanning and three-dimensional data of the human brain, so that accuracy is low; and furthermore, the detection in the prior art relies more on experience of a doctor and the judgment about the examination result, so that a judgment on mild changes in the region of the brain may be inaccurate, nor it is easy to give preventive and therapeutic measures as early as possible.

SUMMARY

One objective of the present disclosure is to provide a method capable of planarizing three-dimensional data of a brain, thereby enabling a more accurate comparison of a diseased brain with a healthy brain on a plane.

According to a first aspect of the present disclosure, there is provided a method of planarizing three dimensional data of a brain implemented by a computer, comprising: acquiring a three-dimensional model of the brain scanned by a scanning device, the three-dimensional model comprising the three-dimensional data of the brain; and mapping, in the computer, the three-dimensional model onto a circle in an area-preserving manner to form an area-preserving map.

According to an embodiment of the present disclosure, the method further comprises: marking a plurality of regions of the three-dimensional model of the brain to distinguish the plurality of regions, wherein the plurality of marked regions are comprised in the area-preserving map.

According to an embodiment of the present disclosure, the method further comprises: mapping the three-dimensional model of the brain onto a unit disc in the area-preserving manner.

According to an embodiment of the present disclosure, the three-dimensional model of the brain is acquired by a nuclear magnetic resonance imaging device.

According to an embodiment of the present disclosure, the method further comprises: removing a brainstem part of the brain from the three-dimensional model.

According to an embodiment of the present disclosure, the method further comprises: performing topology repair on the acquired three-dimensional model.

According to an embodiment of the present disclosure, the performing topology repair on the acquired three-dimensional model comprises: determining positions of genera in the three-dimensional model; and eliminating the genera to reduce the number of the genera in the three-dimensional model to zero.

According to an embodiment of the present disclosure, the plurality of regions of the three-dimensional model of the brain are marked in different colors.

According to an embodiment of the present disclosure, the mapping, in the computer, the three-dimensional model onto a circle in an area-preserving manner to form an area-preserving map comprises: determining a boundary of the circle; harmonically mapping the three-dimensional data to an interior of the boundary to form harmonic mapping points; calculating second weights of the harmonic mapping points, and further calculating a weighted Voronoi diagram of the harmonic mapping points; and mapping the three-dimensional model to the circle in the area-preserving manner according to the weighted Voronoi diagram.

According to an embodiment of the present disclosure, the determining a boundary of the circle comprises: determining a closed curve L in the three-dimensional model; storing points in the L into a linked list vlist, where vlist={$v_0, v_1, \ldots, v_{\{n-1\}}$}, $v_0$ and $v_n$ are one same point; and calculating a length S of the L:

$$s = \sum_{i=0}^{n-1} l_{v_i, v_{i+1}}$$

where $l_{v_i, v_{i+1}}$ is a length of an edge [$v_i, v_{i+1}$]; and
for each $v_i \in$ vlist, performing the following steps: calculating a length $s_i$ from the point $v_0$ to the point $v_i$, where $s_i = \sum_{j=1}^{i} l_{v_{j-1}, v_j}$; according to an angle $\theta_i$ of the point $v_i$, where $$\theta_i = 2\pi \frac{s_i}{s},$$

determining a coordinate $\vec{f}(v_i) = (\cos \theta_i, \sin \theta_i)$ of each point.

According to an embodiment of the present disclosure, the harmonically mapping the three-dimensional data to an interior of the boundary to form harmonic mapping points comprises: initializing the three-dimensional data to form mapping points in the circle; calculating a harmonic energy between the mapping points in the circle; when the harmonic energy is greater than a preset energy gradient threshold, adjusting coordinates of the mapping points, and calculating the harmonic energy according to the adjusted coordinates of the mapping points, and stopping the adjustment until the harmonic energy is less than the preset energy gradient threshold; and taking, as the harmonic mapping points, coordinates of the mapping points when the adjustment is stopped.

According to an embodiment of the present disclosure, the calculating a harmonic energy between the mapping points in the circle comprises: calculating a square value of differences between positions of adjacent mapping points; calculating a first product of the square value and a first weight of an edge formed by the adjacent mapping points; and calculating a sum of the first products for all the mapping points.

According to an embodiment of the present disclosure, the square value and the first weight of the edge formed by the adjacent mapping points are calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

According to an embodiment of the present disclosure, the calculating second weights of the harmonic mapping points and further calculating a weighted Voronoi diagram of the harmonic mapping points comprises: initializing the second weight of each harmonic mapping point, wherein at least three harmonic mapping points form one initial face; determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmonic mapping point, and readjusting the weighted Voronoi diagram according to the updated second weight.

According to an embodiment of the present disclosure, the updating the second weight of each harmonic mapping point comprises: determining an area $A_i$ of an initial face of each harmonic mapping point; determining an area $A_i'$ of a dual face of each harmonic mapping point; determining an area gradient $g_i=A_i-A_i'$ of each harmonic mapping point; determining a sum of squares of the area gradients of all the harmonic mapping points; and if the sum of squares is greater than a preset weight threshold, decreasing the second weight until the sum of squares is less than the weight threshold.

According to an embodiment of the present disclosure, the mapping the three-dimensional model onto the circle in the area-preserving manner according to the weighted Voronoi diagram comprises: determining a center of gravity of each dual face in the weighted Voronoi diagram; mapping each of the harmonic mapping points to the center of gravity of each dual face, thereby mapping the three-dimensional model to the circle in the area-preserving manner.

According to a second aspect of the present disclosure, there is provided a device for planarizing three dimensional data of a brain, comprising: a processor; a memory connected with the processor, the memory having stored therein computer program code which, when executed, causes the processor to perform the method as described above.

According to a third aspect of the present disclosure, there is provided a computer-readable storage medium having stored thereon computer-readable instructions which, when executed by one or more processors, implement the method as described above.

Through the technical solutions of the present disclosure, the three-dimensional brain model can be converted into the circle of the two-dimensional plane, and preferably, mapped onto the unit disc, so that the brain model can be compared with a reference brain model, to facilitate a doctor to more accurately judge a part and degree of a brain lesion.

BRIEF DESCRIPTION OF THE DRAWINGS

With reference to the accompanying drawings, the above features of the present disclosure can be better understood and its numerous objectives, features, and advantages are obvious to those skilled in the art, in which identical reference numerals refer to identical elements, and in which:

FIG. 8 shows a schematic diagram of calculating a weight of each edge:

FIG. 9 shows a flow diagram of calculating second weights of harmonic mapping points, and further calculating a weighted Voronoi diagram of the harmonic mapping points according to an embodiment of the present disclosure;

FIG. 1l shows a flow diagram of mapping a three-dimensional model to a unit disc in an area-preserving manner according to an embodiment of the present disclosure;

DETAILED DESCRIPTION

Technical solutions in embodiments of the present disclosure will be clearly and completely described below with reference to the drawings in the embodiments of the present disclosure. It is obvious that the embodiments described are only some of the embodiments of the present disclosure, not all of them. Based on the embodiments in the present disclosure, all other embodiments, which can be obtained by those skilled in the art without making any creative effort, fall within the protection scope of the present disclosure.

It should be understood that terms "first", "second", "third", and "fourth", etc. in the claims, description, and drawings of the present disclosure are used for distinguishing different objects, rather than describing a specific order. Terms "comprise" and "include" used in the description and claims of the present disclosure, indicate the presence of stated features, whole, steps, operations, elements, and/or components, but do not preclude the presence or addition of one or more other features, whole, steps, operations, elements, components, and/or combination thereof.

It should also be understood that terms used in the description of the present disclosure herein is for the purpose of describing specific embodiments only, but is not intended to limit the present disclosure. As used in the description and claims of this disclosure, "a", "an" and "the" in the singular form are intended to include the plural form, unless other circumstances are clearly indicated in the context. It should be further understood that a term "and/or" used in the description and claims of this disclosure refers to any and all possible combinations of one or more of associated listed items and comprises these combinations.

As used in the description and claims, a term "if" can be interpreted contextually as "when" or "once" or "in response to determining" or "in response to detecting". Similarly, a phrase "if determining" or "if detecting [a described condition or event]" can be interpreted contextually as meaning "once determining" or "in response to determining" or "once detecting [a described condition or event]" or "in response to detecting [a described condition or event]".

The specific embodiments of the present disclosure are described in detail below in conjunction with the accompanying drawings.

Figure 1:
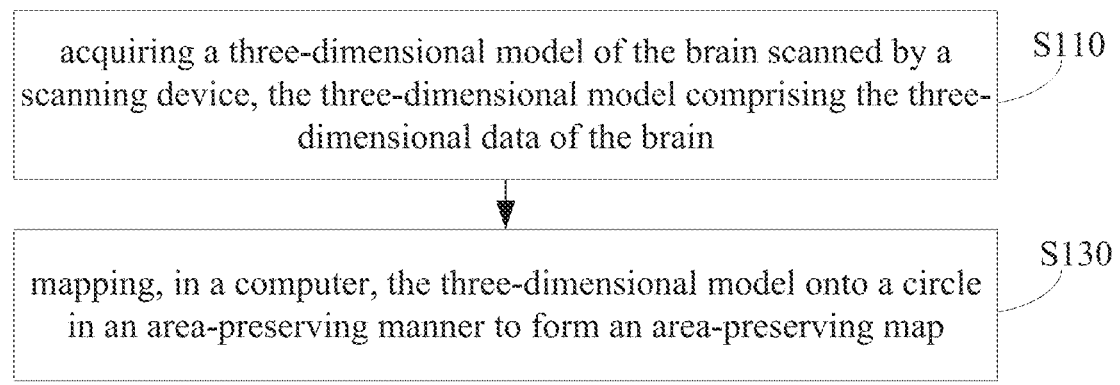
FIG. 1 shows a flow diagram of a method of planarizing three-dimensional data of a brain according to an aspect of the present disclosure.

FIG. 1 shows a flow diagram of a method of planarizing three-dimensional data of a brain, comprising: step S110, acquiring, a three-dimensional model of the brain scanned by a scanning device, the three-dimensional model comprising the three-dimensional data of the brain; and step S130, mapping, in a computer, the three-dimensional model onto a circle in an area-preserving manner to form an area-preserving map.

The brain is the most advanced part of the nervous system and consists of left and right cerebral hemispheres, between which transverse nerve fibers are associated. On a surface of the human brain are many concave sulci (fissures), between which there are convex gyri, so that an area of the cerebral cortex is greatly increased.

The brain is divided into a plurality of different regions, each of which can have a different function that plays a vital role in human's consciousness, spirit, language, learning, memory, intelligence, limb actions and the like. If some parts of the brain are damaged or diseased, the human's behavior, language and memory will be directly affected. Taking an Alzheimer's disease as an example, a cerebral cortex of a patient atrophies, and damaged regions comprise a thought region, a planning region and a memory region; hippocampus is a main region for forming a new memory and is also a region where special severe atrophy occurs; and a fluid-filled space in a ventricle will become larger.

It should be understood that the brain described herein is a physical entity that exists in reality and the three-dimensional model of the brain is a digital representation of the brain, wherein the three-dimensional model can be read, analyzed, processed by the computer, and based on these analysis and processing results, a desired result can be obtained.

In order to accurately analyze lesions of various parts of the brain, the three-dimensional brain model can be, in an area-preserving form, mapped onto a circle, or called a circular plane. The area-preserving mapping has less impact on an area (or a ratio of the area to the total area) of a target object, which is more beneficial to the subsequent judgment. The mapping here is to directly map the three-dimensional data onto the plane without an intermediate change or the like.

The three-dimensional model of the brain can be acquired in a number of ways, for example, by a nuclear magnetic resonance imaging device, CT, or the like.

Figure 2:
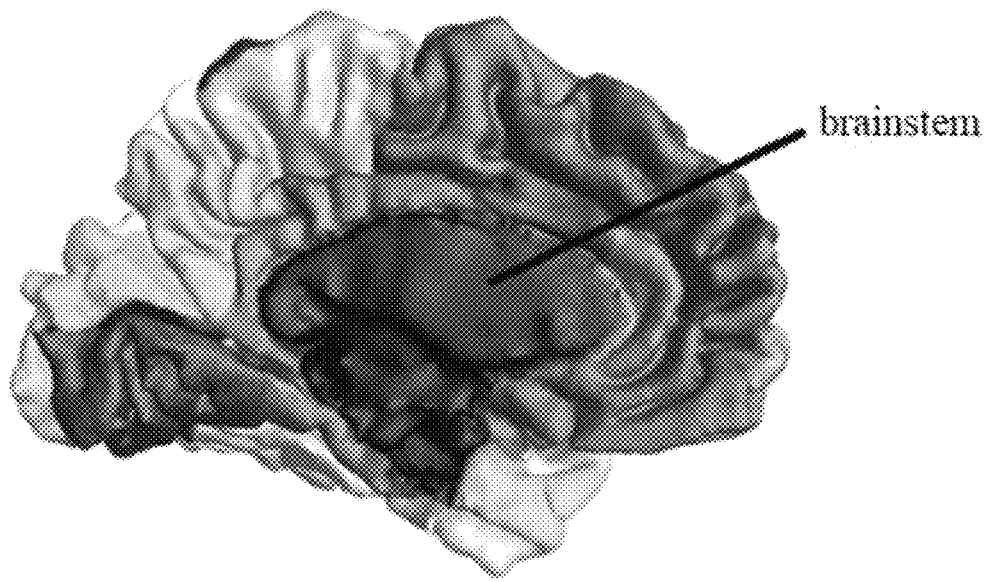
FIG. 2 shows a schematic diagram of a brain where a brainstem part is removed according to an embodiment of the present disclosure.

In the analysis of the three-dimensional image, a part that is not concerned can be removed from the three-dimensional model of the brain to exclude an impact of the part that is not concerned on the result. For example, a brainstem part, which typically comprises midbrain, pons and medulla oblongata, can be removed. FIG. 2 shows a schematic diagram of a brain where a brainstem part is removed according to an embodiment of the present disclosure. It should be understood that although the brainstem is taken as an example in the present disclosure to describe the part to be removed, those skilled in the art can remove any part of the brain as desired.

In general, there will be more noise in the formed three-dimensional model, and the presence of noise will also affect the subsequent further mapping.

Figure 3:
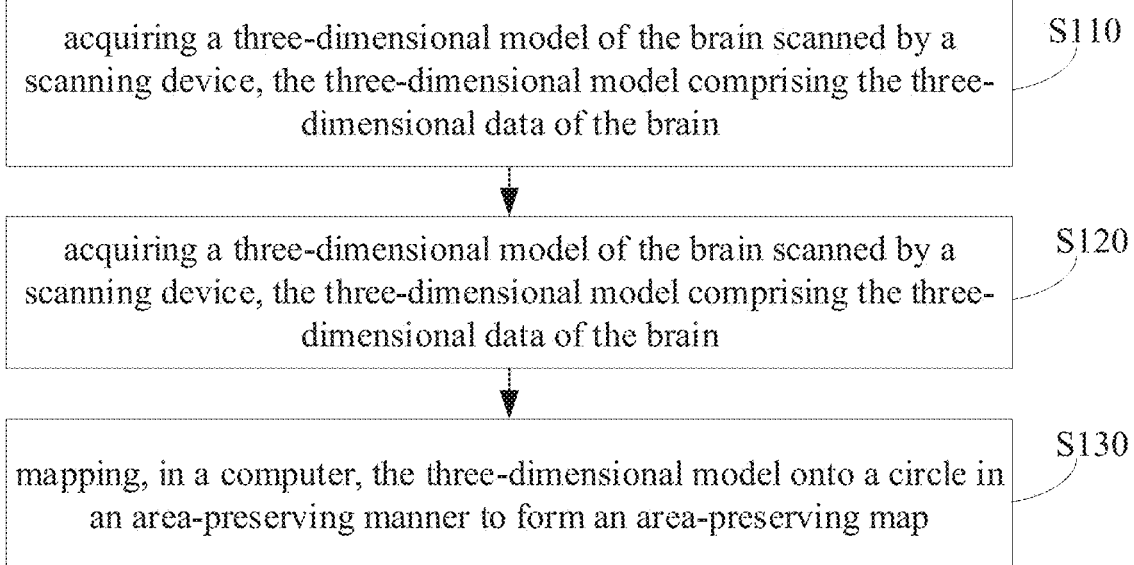
FIG. 3 shows a flow diagram of a method of planarizing three-dimensional data of a brain according to another embodiment of the present disclosure.

According to an embodiment of the present disclosure, as shown in FIG. 3, the present disclosure can further comprise, step S120, performing topology repair on the three-dimensional model. The topology repair is geometric shape repair, to repair the imported model into a curved surface with a closed shape, so that the model becomes a whole. Geometry without topology repair may have face or line missing, or face connection errors.

It can be appreciated that there are typically many false genera (handles and tunnels) in the three-dimensional model due to image segmentation errors. These false genera should be detected and eliminated.

These handles are too tiny to be detected directly by naked eyes. A practical method is to obtain them by methods of calculating topology that usually depend on algorithms of handle loops and tunnel loops of the curved surface. After these false handles are obtained, they are cut along the handle loops, and then gaps are filled to remove topological noise.

Figure 4:
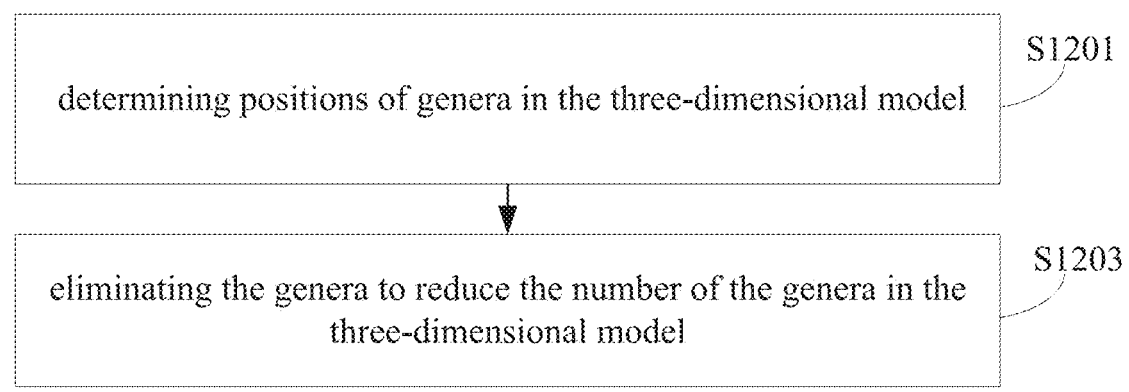
FIG. 4 shows a flow diagram of a method of performing topology repair on a three-dimensional model according to an embodiment of the present disclosure.

According to an embodiment of the present disclosure, as shown in FIG. 4, the performing topology repair on the three-dimensional model comprises: step S1201, determining positions of genera in the three-dimensional model; and step S1203, eliminating the genera to reduce the number of the genera in the three-dimensional model to zero.

The reducing the number of the genera in the three-dimensional model as described above, preferably, is to reduce the number of the genera to zero, i.e., to implement a zero-genus three-dimensional model, which will help to improve the accuracy of mapping the three-dimensional model to the two-dimensional plane.

According to an embodiment of the present disclosure, a plurality of regions of the three-dimensional model of the brain are marked to distinguish the plurality of regions, wherein the plurality of marked regions are comprised in the area-preserving map. The plurality of regions of the three-dimensional model of the brain can be marked in different colors.

Figure 5:
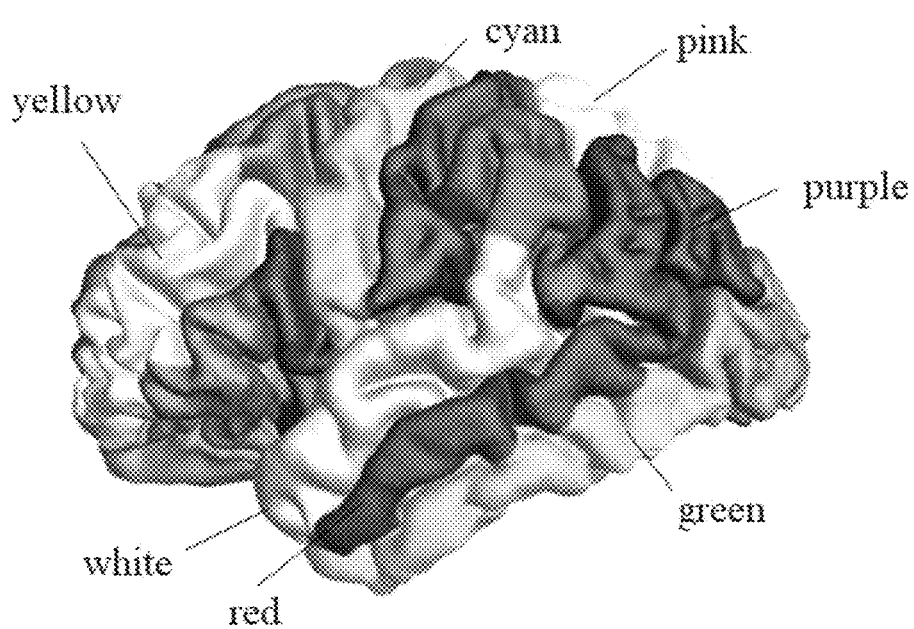
FIG. 5 shows a schematic diagram of marking a plurality of regions of a three-dimensional model of a brain in different colors.

FIG. 5 shows a schematic diagram of marking a plurality of regions of a three-dimensional model of a brain in different colors.

Since the brain has different functional regions, in order to facilitate subsequent check of whether these functional regions change or not, each functional region of the brain can be marked in a variety of ways, for example, each region can be marked with different contour lines, and preferably, the different regions can be marked with different colors, such as red, white, green, yellow, cyan, pink, purple, and the like. An advantage of marking the different regions using the colors is that it is very convenient to compare a two-dimensional view of the patient's brain with a healthy reference two-dimensional view. It should be understood that the above color is merely one example, and the color used can also be a color value that can be recognized by the computer but is not easily distinguished by human.

The method of mapping the three-dimensional model onto the circle in the area-preserving manner is described in detail below.

It should be appreciated that the three-dimensional model can be mapped to the circle in many manners. For example, a three-dimensional model can be mapped to a circle in a conformal manner, but this manner has a certain drawback because the conformal manner will cause area information of the three-dimensional object to be lost, so that information is lost when a two-dimensional image is restored to a three-dimension one again.

In the present disclosure, however, the three-dimensional object is mapped onto the circle in the area-preserving mapping manner, so that areas of all parts in the three-dimensional object are still kept unchanged in the circle, to facilitate the subsequent further processing.

Preferably, according to an embodiment of the present disclosure, the three-dimensional model of the brain can be mapped onto a unit disc in the area-preserving manner.

Further, in embodiments of the present disclosure, an advantage of mapping three-dimensional models of different brains onto the unit disc is that, considering that each person's brain is different in size, if each brain is only mapped onto a two-dimensional plane without a uniform size, there may be a great difference between sizes of a brain on each two-dimensional plane and a healthy reference two-dimensional view, which is inconvenient to perform comparison. The three-dimensional models of all the brains are mapped onto the unit circle, which facilitates the formation of a uniform comparison standard.

It should be understood that the unit disc described herein refers to, under Euclidean metric, a circle with an area of Pi, i.e., a radius of 1. As described above, mapping all three-dimensional data onto the two-dimensional disc of a uniform size facilitates the subsequent further comparison.

It should be understood that although the step S120 shown in FIG. 3 is before the step S130, the order of the two can be exchanged, that is, after the plurality of regions of the three-dimensional model of the brain are marked, the topology repair is performed on the three-dimensional model.

Figure 6:
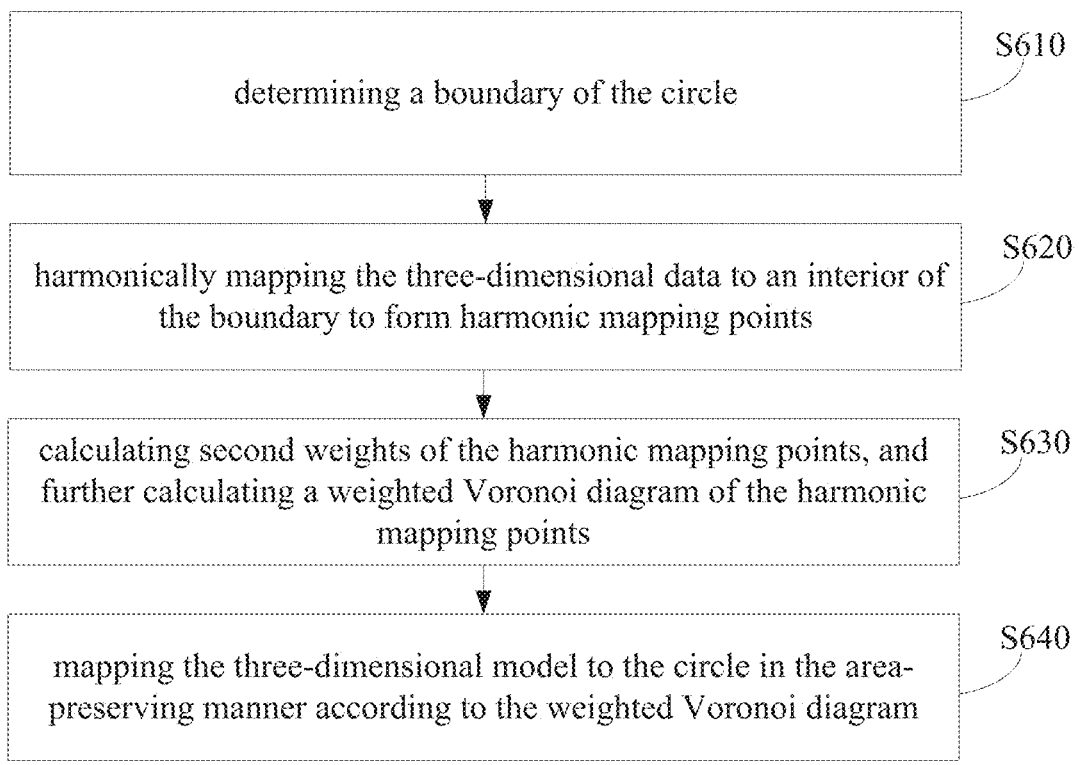
FIG. 6 shows a schematic flow diagram of mapping a three-dimensional model of a brain onto a circle in an area-preserving manner to form an area-preserving map according to an embodiment of the present disclosure.

FIG. 6 shows a schematic flow diagram of mapping the three-dimensional model of the brain onto a circle in an area-preserving manner to form an area-preserving map according to an embodiment of the present disclosure, comprising, step S610, determining a boundary of the circle; step S620, harmonically mapping the three-dimensional data to an interior of the boundary to form harmonic mapping points; step S630, calculating second weights of the harmonic mapping points, and further calculating a weighted Voronoi diagram of the harmonic mapping points; and step S640, mapping the three-dimensional model to the circle in the area-preserving manner according to the weighted Voronoi diagram.

According to an embodiment of the present disclosure, the determining a boundary of the circle comprises: determining a closed curve L in the three-dimensional model; storing points in the L into a linked list vlist, where vlist=$\{v_0, v_1, \ldots, v_{\{n-1\}}\}$, $v_0$ and $v_n$ are one same point, and calculating a length S of the L by:

$$s = \sum_{i=0}^{n-1} l_{v_i, v_{i+1}}$$

where $l_{v_i, v_{i+1}}$ is a length of an edge $[v_i, v_{i+1}]$; and for each $v_i \in$ vlist, performing the following steps: calculating a length $s_i$ from a point $v_0$ to the point $v_i$, where $s_i = \sum_{j=1}^{i} l_{v_{j-1}, v_j}$; calculating an angle $\theta_i$ of the point $v_i$, where $$\theta_i = 2\pi \frac{s_i}{s};$$

determining a coordinate of each point $\vec{f}(v_i) = (\cos \theta_i, \sin \theta_i)$; and normalizing the curve as the boundary of the circle.

It can be seen from the above that the determined boundary of the circle is actually a boundary of a polygon, and the more sampling points are taken, the closer the polygon is to the circle.

It can also be seen from the above that the above coordinate of the point is actually one polar coordinate. It should be understood that the polar coordinate is only one way, and any other type of coordinate system can also be adopted.

After the boundary is determined, points in the three-dimensional data that are non-boundary can be mapped to the interior of the circle defined by the boundary. These three-dimensional data can be mapped onto the circle by means of the harmonic mapping.

Expressed in a popular way, when the three-dimensional model is mapped to the circle, interior parts of the model can also, in themselves, receive certain tensile force due to deformation of the boundary and then spread towards the boundary, and a spreading direction of each point is a result of a resultant force of all points around the point. Until each part no longer changes, it amounts to reaching a "harmonic" state.

Preferably, although it is given in the above that after the harmonic mapping is completed, the two-dimensional plane formed by the mapping is normalized to the unit disc; however, in another embodiment of the present disclosure, when the boundary is formed, a perimeter of the boundary is set to 2Pi, that is, no matter what the length S of L is, it is first adjusted to 2Pi in equal proportion, and the harmonic mapping is performed in the above unit disc formed.

Figure 7:
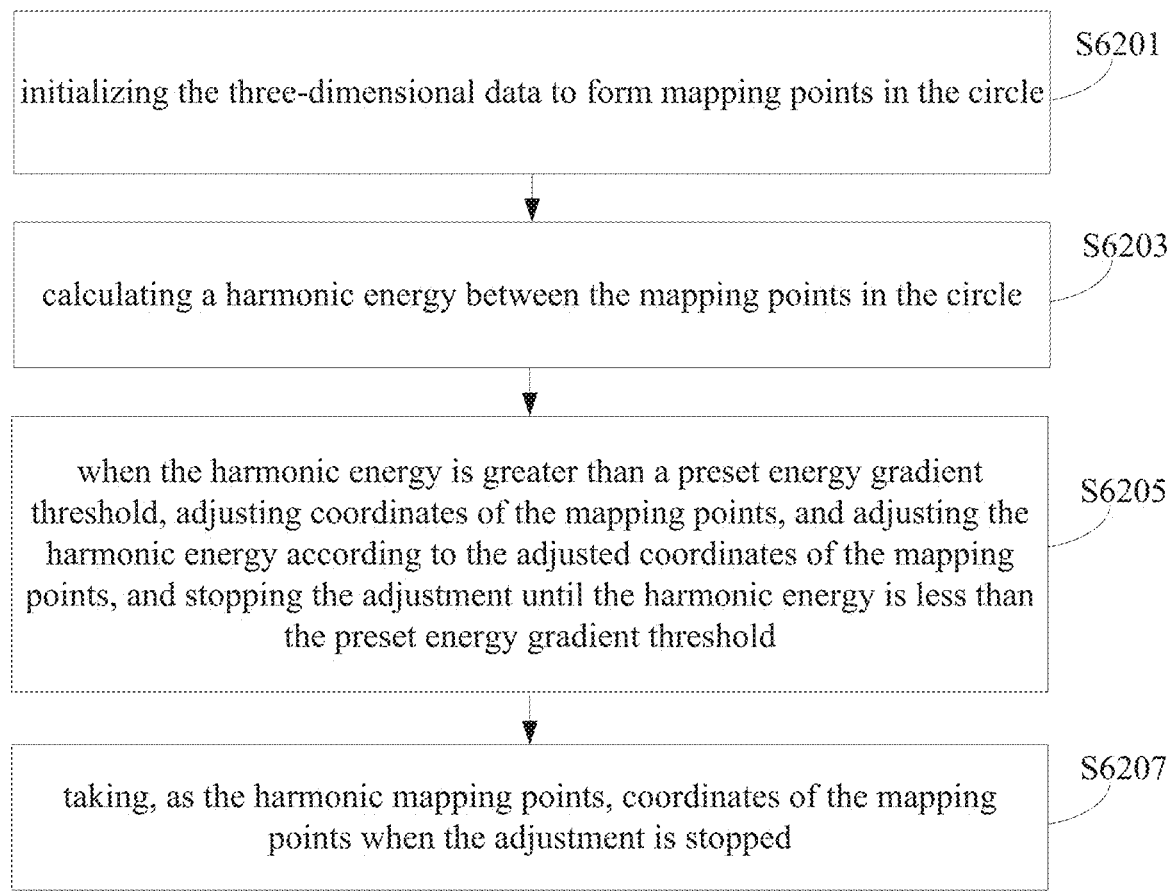
FIG. 7 shows a flow diagram of harmonically mapping three-dimensional data into an interior of a boundary to form harmonic mapping points.

FIG. 7 shows a flow diagram of harmonically mapping three-dimensional data to an interior of a boundary to form harmonic mapping points.

As shown in FIG. 7, the harmonically mapping the three-dimensional data to an interior of the boundary to form harmonic mapping points S620 comprises: step S6201, initializing the three-dimensional data to form mapping points in the circle; step S6203, calculating a harmonic energy between the mapping points in the circle; step S6205, when the harmonic energy is greater than a preset energy gradient threshold, adjusting coordinates of the mapping points, and adjusting the harmonic energy according to the adjusted coordinates of the mapping points, and stopping the adjustment until the harmonic energy is less than the preset energy gradient threshold; and step S6207, taking, as the harmonic mapping points, coordinates of the mapping points when the adjustment is stopped.

It should be understood that the above boundary can be the boundary formed by the L, or the boundary formed after the length S of the L is adjusted to 2Pi.

The above steps are specifically described below.

For a mesh M, the energy gradient threshold δE is preset.

For a non-boundary point, it is initialized to $\vec{f}=(0,0)$, where the $\vec{f}$ represents a position of the point in the circle. According to an embodiment of the present disclosure, all the three-dimensional data points can be mapped onto the above circle, and initially, all the three-dimensional points can be mapped to a position (0, 0), which is, of course, only one example, and initially, all the three-dimensional points can also be mapped into the circle evenly, i.e., all the points are equidistant in the circle.

Next, an initial harmonic energy E is calculated, i.e. the harmonic energy between the above mapping points in the circle is calculated. A harmonic energy can be calculated as follows:

$$E(f)=\Sigma_{[v_i,v_j]\in M} k_{ij}(f(v_j)-f(v_i))^2 \qquad \text{Equation 1}$$

In the above equation, E (f) represents the harmonic energy of all the mapping points; it can be understood that the initial harmonic energy may be maximum, and thereafter the position of each mapping point will be gradually adjusted so that the harmonic energy gradually decreases and finally falls below one preset energy gradient threshold. At this time, the harmonic state can be reached.

In the above equation, the energy between all the points belonging to the circle (excluding the boundary points) and their adjacent points is calculated; according to an embodiment of the present disclosure, the calculating a harmonic energy between the mapping points in the circle comprises: firstly, calculating a square value of differences between positions of adjacent mapping points; calculating a first product of the square value and a first weight of an edge formed by the adjacent mapping points; and calculating a sum of the first products for all the mapping points to obtain the initial harmonic energy.

If the initial harmonic energy is greater than the energy gradient threshold, the positions of the corresponding points are adjusted and a new harmonic energy E is recalculated, and the harmonic energy calculated in the previous round is set as $E_0$.

Next, a difference between the new harmonic energy E and the harmonic energy $E_0$ calculated in the previous round is calculated, i.e., whether |E−$E_0$| is greater than the preset harmonic energy gradient δE. This cycle is continued until the difference between the new harmonic energy E and the harmonic energy $E_0$ calculated in the previous round is not greater than the preset harmonic energy gradient threshold δE. At this time, the energy gradient between all the points is minimum, and the harmonic state is reached.

The coordinate of each mapping point can be calculated by the following equation:

$$\vec{f}(v_i) = \sum_{[v_i,v_j]\in M} \frac{k_{ij}\vec{f}(v_j)}{\Sigma_j k_{ij}} \qquad \text{Equation 2}$$

where $v_i$ is a representation of the i-th point, $v_j$ is a representation of the j-th point adjacent to i, $f(v_i)$ represents a position of the point $v_i$, and M represents a triangular mesh curved surface, $k_{ij}$ is a weight of an edge $[v_i, v_j]$.

According to an embodiment of the present disclosure, the square value and the first weight of the edge formed by the adjacent mapping points are calculated by: determining an angle of a triangle that corresponds to the edge; if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

For the triangular mesh, there are generally two cases for triangle's edges, wherein one is an edge common to two triangles and the other is an edge of the boundary, as shown in FIG. 8.

In FIG. 8, an edge determined by points i and j is an edge common to two triangles, and an edge determined by points i and l is an edge of the boundary, angles of the two triangles that correspond to the edge $e_{ij}$ are α and β, respectively, and an angle of a triangle that corresponds to the edge $e_{il}$ is γ, and therefore, weights of the two edges are respectively calculated by:

$k_{ij}=\omega(e_{ij})=\frac{1}{2}(\cot \alpha+\cot \beta)$ edge of the interior (having two adjacent faces)

$k_{il}=\omega(e_{il})=\frac{1}{2} \cot \gamma$ edge of the boundary (having only one face)

It can be seen that as the positions of the points are continuously adjusted, the angle of each triangle continuously changes, and therefore the weight of the edge continuously changes. But due to the convergence of this adjustment, the weight of the edge will gradually remain constant, so that the mapping of the image reaches the harmonic state.

In other words, it can be seen from the above that, with the adjustment of each mapping point, the harmonic energy gradually decreases, and eventually reaches less than the specific harmonic energy gradient threshold, thereby realizing the harmonic mapping.

FIG. 9 shows a flow diagram of calculating second weights of harmonic mapping points, and further calculating a weighted Voronoi diagram of the harmonic mapping points according to an embodiment of the present disclosure.

As shown in FIG. 9, in the present disclosure, the calculating second weights of the harmonic mapping points, and further calculating a weighted Voronoi diagram of the harmonic mapping points comprises: step S6301, initializing the second weight of each harmonic mapping point, wherein at least three harmonic mapping points form one initial face; step S6303, determining weighted dual points of each initial face, the weighted dual points having equal weighted distances to vertices of each initial face, wherein the weighted dual points are connected to form a dual face of the weighted dual points, and a plurality of weighted dual faces determine a weighted Voronoi diagram; and, step S6305, updating the second weight of each harmonic mapping point and readjusting the weighted Voronoi diagram according to the updated second weight.

Figures 10, 11:
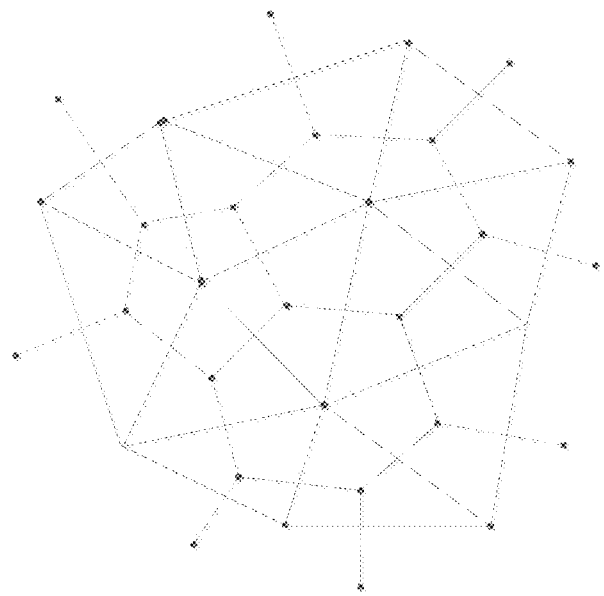
FIG. 10 shows an example of a Voronoi diagram.

First, according to an embodiment of the present disclosure, the weighted Voronoi diagram is determined on the basis of the formed harmonic mapping points. FIG. 10 shows an example of a Voronoi diagram.

As shown in FIG. 10, the Voronoi diagram is a dual form of a mesh (not limited to the triangular mesh), and taking the triangular mesh as an example, for each face in the mesh, it corresponds to one dual point (vertex of a dotted line) in the Voronoi diagram, the dual point has equal distances to three vertices (i.e., the harmonic mapping points in the above, vertices of solid lines in FIG. 10), and each point (harmonic mapping point in the present disclosure) in the original mesh also corresponds to one dual face in the Voronoi diagram, as shown in FIG. 10. However, the weighted Voronoi diagram is different from an ordinary Voronoi diagram in that each point in the original mesh has a weight, and the distance is calculated originally by $d=\|v-q\|^2$, and after the weighting, by $d=\|v-q\|^2+\omega$, so that the adding of the weight $\omega$ will make a size of a Voronoi cell change with the weight. The greater weight a vertex of a certain face has, the farther Euclidean distance a circumcenter of the face has to the vertex, so that an area of a dual face corresponding to the vertex will become larger.

The method in FIG. 9 is specifically explained below.

According to an embodiment of the present disclosure, the updating the second weight of each harmonic mapping point comprises: determining an area $A_i$ of an initial face of each harmonic mapping point; determining an area $A_i'$ of a dual face of each harmonic mapping point; determining an area gradient $g_i=A_i-A_i'$ of each harmonic mapping point; determining a sum of squares of the area gradients of all the harmonic mapping points, and if the sum of squares is greater than a preset weight threshold, decreasing the second weight until the sum of squares is less than the weight threshold.

First, a weight of each point is initialized to $\omega_i=0$, and the weight threshold $\varepsilon$ is given, for example, $\varepsilon=10^{-3}$.

For each face $f_i=[v_a, v_b, v_c]$ in M, its weighted dual point $q_i$ is calculated using the following system of equations, where $v_a$, $v_b$, $v_c$ represent three vertices of each solid-line triangle:

$$\begin{cases} 2(v_a - v_b)^T q_i = \|v_a\|^2 - \|v_b\|^2 + \omega_a - \omega_b \\ 2(v_b - v_c)^T q_i = \|v_b\|^2 - \|v_c\|^2 + \omega_b - \omega_c \end{cases} \quad \text{Equation 3}$$

i.e., $q_i$ has equal weighted distances d to these three points, and $d(q,v)=|v-q|^2+\omega_v$.

$d(q,v)$ is a weighted distance of q and v, and $\omega_v$ is a weight of a point v.

For each solid-line edge in the M, dual points q on both sides of the solid-line edge are connected to form a new dotted-line edge as a dual edge of the solid-line edge.

A new diagram formed by these dual edges is the weighted Voronoi diagram $\Omega$. Each harmonic mapping point, in the weighted Voronoi diagram $\Omega$, corresponds one dual face, which is one cell $\text{Cell}_i$, then a current area of each point is $A_i'=\text{area}(\text{Cell}_i)$.

A gradient $g_i=A_i-A_i'$ of each point is calculated, and let $G=\{g_0, g_1, \ldots, g_n\}$, if $\|G\|^2<\varepsilon$, iterative updating is stopped, otherwise, let $w_i=\omega_i-\lambda g_i$, where $\lambda$ is a step of the gradient descent, needs manual setup, and is generally set to be a value less than 1, and a new weight can also be iteratively calculated using a Newton method and the like. $A_i$ is a target area of each harmonic mapping point, i.e., an area in the three-dimensional object that the harmonic mapping point corresponds to.

FIG. 11 shows a flow diagram of mapping the three-dimensional model to a circle in an area-preserving manner according to an embodiment of the present disclosure.

According to an embodiment of the present disclosure, the mapping the three-dimensional model to the circle in the area-preserving manner according to the weighted Voronoi diagram comprises: step S6401, determining a center of gravity of each dual face in the weighted Voronoi diagram; and step S6403, mapping each of the harmonic mapping points to the center of gravity of each dual face, thereby mapping the three-dimensional model to the circle in the area-preserving manner.

Therefore, in this way, the three-dimensional data of the brain can be mapped onto the circle in the area-conserving manner.

Figure 12:
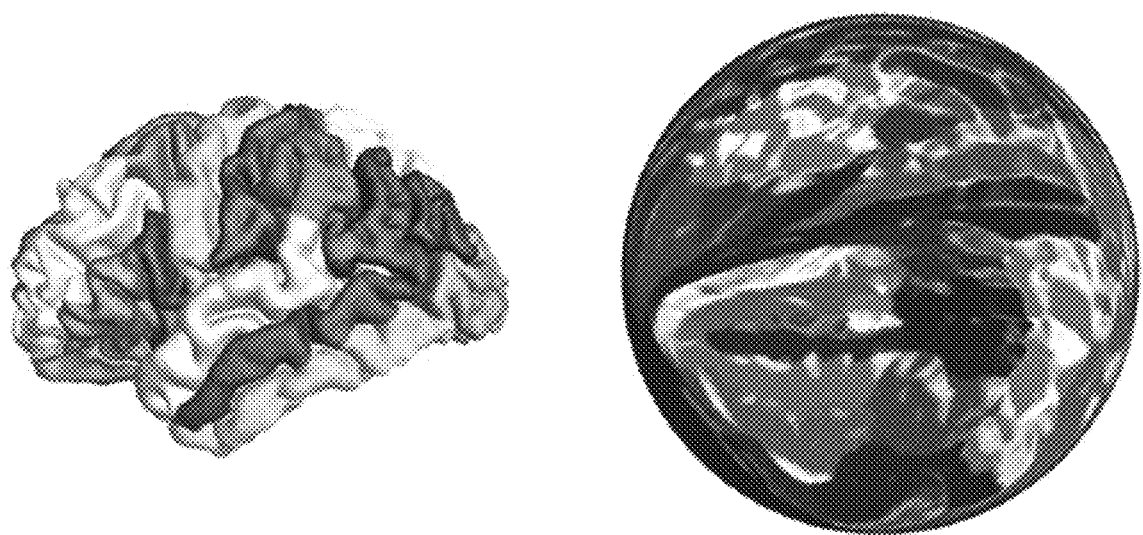
FIG. 12 shows a schematic diagram of mapping a brain to a unit disc according to an embodiment of the present disclosure.

FIG. 12 shows a schematic diagram of mapping a brain to a unit disc according to an embodiment of the present disclosure.

It should be appreciated that mapping the brain to the circle is essentially the same as mapping the brain to the unit disc, but the mapping the brain to the unit disc facilitates a more intuitive comparison of brains of different sizes.

As shown in FIG. 12, the three-dimensional brain is mapped onto the two-dimensional unit disc, each part of the brain is planarized to a different part of the disc, and since each part of the brain is marked by a different color, each part of the brain on the plane is also represented in a different color. By comparing the mapped unit disc with a reference unit disc, it is clear which part of the brain has changed, and therefore, it is further determined what disease the changing part may suffer.

According to a second aspect of the present disclosure, there is provided a device for planarizing three dimensional data of a brain, comprising: a processor; a memory connected with the processor, the memory having stored therein computer program code which, when executed, causes the processor to perform the method as described above.

According to a third aspect of the present disclosure, there is provided a computer-readable storage medium having stored thereon computer-readable instructions which, when executed by one or more processors, implement the method as described above.

Exemplary Device

It can be appreciated by those skilled in the art that, various aspects of the present disclosure can be implemented as a system, method or program product. Accordingly, the various aspects of the present disclosure can be specifically implemented in the following form: an entire hardware embodiment, an entire software embodiment (comprising firmware, microcode, etc.), or an embodiment combining hardware and software aspects, which can be collectively called a "circuit", "module", or "system" herein.

In some possible embodiments, a device for testing an application according to an embodiment of the present disclosure can comprise at least one processing unit, and at least one storage unit. The storage unit has stored therein program code which, when executed by the processing unit, causes the processing unit to perform the steps in the method of testing the application according to various exemplary embodiments of the present disclosure as described in the above "exemplary method" section of this specification.

Exemplary Program Product

In some possible embodiments, the various aspects of the present disclosure can also be implemented in a form of a program product comprising program code which, when the program product is run on the device, causes the device to perform the steps in the method of testing the application according to various exemplary embodiments of the present disclosure as described in the above "exemplary method" section of this specification.

The program product can employ any combination of one or more readable media. The readable medium can be a readable signal medium or a readable storage medium. The readable storage medium can be, for example, but is not limited to, an electronic, magnetic, optical, electromagnetic, infrared, or semiconductor system, apparatus, or device, or any combination of the above. More specific examples (a non-exhaustive list) of the readable storage medium comprise: an electrical connection having one or more wires, a portable diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the above.

The readable signal medium can comprise a data signal propagated in baseband or as part of a carrier wave, in which readable program code is carried. Such a propagated data signal can take a variety of forms, comprising, but not limited to, an electro-magnetic signal, an optical signal, or any suitable combination of the above. The readable signal medium can also be any readable medium other than the readable storage medium, wherein the readable medium can send, propagate, or transmit a program for use by or in conjunction with an instruction execution system, apparatus, or device.

Program code contained on the readable medium can be transmitted using any appropriate medium, comprising but not limited to wireless, wired, optical cable, RF, etc., or any suitable combination of the above.

Program code for performing operations of the present disclosure can be written in any combination of one or more programming languages, wherein the programming language comprises an object-oriented programming language such as Java, C++ or the like and also comprises a conventional procedural programming language such as the "C" programming language or a similar programming language. The program code can be executed entirely on a user computing device, partly on the user computing device and partly on a remote computing device, or entirely on the remote computing device or a server. In the case where the remote computing device is involved, the remote computing device can be connected to the user computing device through any kind of network, comprising a local area network (LAN) or a wide area network (WAN), or can be connected to an external computing device (e.g., through the Internet using an internet service provider).

It should be noted that although several units or sub-units of the device are mentioned in the above detailed description, such a division is merely illustrative and not mandatory. In fact, features and functions of two or more units described above can be embodied in one unit according to the embodiments of the present disclosure. Conversely, features and functions of one unit described above can be further divided and embodied in a plurality of units.

Furthermore, while operations of the methods of the present disclosure are depicted in the drawings in a specific order, this does not require or imply that these operations must be performed in this specific order, or that all of the illustrated operations must be performed, to achieve desirable results. Additionally or alternatively, certain steps can be omitted, multiple steps can be combined into one step for execution, and/or one step can be broken down into multiple steps for execution.

While the spirit and principles of the present disclosure have been described with reference to several specific embodiments, it should be understood that the present disclosure is not limited to the disclosed embodiments, and the division of various aspects does not mean that the features in these aspects cannot be combined to benefit, but is only for the convenience of expression. The present disclosure is intended to cover various modifications and equivalent arrangements included within the spirit and scope of the attached claims.

What is claimed is:

1. A method of planarizing three dimensional data of a brain implemented by a computer, the method comprising:
    acquiring, a three-dimensional model of the brain scanned by a scanning device, the three-dimensional model comprising the three-dimensional data of the brain; and
    mapping, in the computer, the three-dimensional model onto a circle in an area-preserving manner to form an area-preserving map,
    wherein the mapping, in the computer, the three-dimensional model onto the circle in the area-preserving manner to form the area-preserving map comprises:
    determining a boundary of the circle;
    harmonically mapping the three-dimensional data to an interior of the boundary to form harmonic mapping points;
    calculating second weights of the harmonic mapping points, and further calculating a weighted Voronoi diagram of the harmonic mapping points; and
    mapping the three-dimensional model to the circle in the area-preserving manner according to the weighted Voronoi diagram.

2. The method of claim 1, further comprising:
    marking a plurality of regions of the three-dimensional model of the brain to distinguish the plurality of regions, wherein the plurality of marked regions are comprised in the area-preserving map.

3. The method of claim 2, wherein the plurality of regions of the three-dimensional model of the brain are marked in different colors.

4. The method of claim 1, further comprising:
    mapping the three-dimensional model of the brain onto a unit disc in the area-preserving manner.

5. The method of claim 1, wherein the three-dimensional model of the brain is acquired by a nuclear magnetic resonance imaging device.

6. The method of claim 1, further comprising:
    removing a brainstem part of the brain from the three-dimensional model.

7. The method of claim 1, further comprising:
    performing topology repair on the acquired three-dimensional model.

8. The method of claim 7, wherein the performing topology repair on the acquired three-dimensional model comprises:
    determining positions of genera in the three-dimensional model; and
    eliminating the genera to reduce the number of the genera in the three-dimensional model to zero.

9. The method of claim 1, wherein the determining a boundary of the circle comprises:
    determining a closed curve L in the three-dimensional model;

storing points in the L into a linked list vlist, where vlist=$\{v_0, v_1, \ldots, v_{\{n-1\}}\}$, $v_0$ and $v_n$ are one same point;

calculating a length S of the L:

$$s = \sum_{i=0}^{n-1} l_{v_i, v_{i+1}}$$

where $l_{v_i, v_{i+1}}$ is a length of an edge $[v_i, v_{i+1}]$; and for each $v_i \in$ vlist, performing the following steps:

calculating a length $s_i$ from the point $v_0$ to the point $v_i$, where $s_i = \sum_{j=1}^{i} l_{v_{j-1} v_j}$;

according to an angle $\theta_i$ of the point $v_i$, where $$\theta_i = 2\pi \frac{s_i}{s},$$

determining a coordinate $\vec{f}(v_i) = (\cos \theta_i, \sin \theta_i)$ of each point.

10. The method of claim 1, wherein the harmonically mapping the three-dimensional data to an interior of the boundary to form harmonic mapping points comprises:

initializing the three-dimensional data to form mapping points in the circle;

calculating a harmonic energy between the mapping points in the circle;

when the harmonic energy is greater than a preset energy gradient threshold, adjusting coordinates of the mapping points, and calculating the harmonic energy according to the adjusted coordinates of the mapping points, and stopping the adjustment until the harmonic energy is less than the preset energy gradient threshold; and taking, as the harmonic mapping points, coordinates of the mapping points when the adjustment is stopped.

11. The method of claim 10, wherein the calculating a harmonic energy between the mapping points in the circle comprises:

calculating a square value of differences between positions of adjacent mapping points;

calculating a first product of the square value and a first weight of an edge formed by the adjacent mapping points; and calculating a sum of the first products for all the mapping points.

12. The method of claim 11, wherein the square value and the first weight of the edge formed by the adjacent mapping points are calculated by:

determining an angle of a triangle that corresponds to the edge;

if the edge is an edge common to two triangles, the first weight of the edge being equal to half of a sum of cotangent trigonometric functions of angles that are opposite to the edge in the two triangles; and if the edge is an edge on the boundary, the first weight of the edge being equal to half of a cotangent trigonometric function of an angle that is opposite to the edge in a triangle where the edge is located.

13. The method of claim 1, wherein the calculating second weights of the harmonic mapping points and further calculating a weighted Voronoi diagram of the harmonic mapping points comprises:

initializing the second weight of each harmonic mapping point, wherein at least three harmonic mapping points form one initial face;

determining weighted dual points of each initial face, the weighted dual points having equal weighted distances to vertices of each initial face, wherein the weighted dual points are connected to form a dual face of the weighted dual points, and a plurality of dual faces determine a weighted Voronoi diagram; and updating the second weight of each harmonic mapping point, and readjusting the weighted Voronoi diagram according to the updated second weight.

14. The method of claim 13, wherein the updating the second weight of each harmonic mapping point comprises:

determining an area $A_i$ of an initial face of each harmonic mapping point;

determining an area $A_i'$ of a dual face of each harmonic mapping point;

determining an area gradient $g_i = A_i - A_i'$ of each harmonic mapping point;

determining a sum of squares of the area gradients of all the harmonic mapping points; and if the sum of squares is greater than a preset weight threshold, decreasing the second weight until the sum of squares is less than the weight threshold.

15. The method of claim 13, wherein the mapping the three-dimensional model to the circle in the area-preserving manner according to the weighted Voronoi diagram comprises:

determining a center of gravity of each dual face in the weighted Voronoi diagram; and mapping each of the harmonic mapping points to the center of gravity of each dual face, thereby mapping the three-dimensional model to the circle in the area-preserving manner.

16. A device for planarizing three dimensional data of a brain, comprising:

a processor; and a memory connected with the processor, the memory having stored therein computer program code which, when executed, causes the processor to perform the method of claim 1.

17. A non-transitory computer-readable storage medium having stored thereon computer-readable instructions which, when executed by one or more processors, implement the method of claim 1.

* * * * *